United States Patent [19]

Gargan et al.

[11] Patent Number: 5,223,410
[45] Date of Patent: Jun. 29, 1993

[54] METHOD FOR PRODUCTION OF ANTIBODIES UTILIZING AN ANTIGEN-FREE ANIMAL

[75] Inventors: Paul E. Gargan, Southbend; Victoria A. Ploplis, Southbend; Julian R. Pleasants, Granger, all of Ind.

[73] Assignee: American Biogenetic Sciences, Inc., Copiague, N.Y.

[21] Appl. No.: 835,800

[22] Filed: Feb. 14, 1992

Related U.S. Application Data

[63] Continuation of Ser. No. 364,053, Jun. 8, 1989, Pat. No. 5,120,834, which is a continuation-in-part of Ser. No. 206,259, Jun. 13, 1988, abandoned.

[51] Int. Cl.$^5$ .................... C12P 21/08; C07K 15/00; C07K 15/28
[52] U.S. Cl. .................... 435/70.21; 435/70.1; 530/389.3; 530/388.25
[58] Field of Search .................... 435/70.21, 70.1; 530/389.3, 388.25

[56] References Cited

PUBLICATIONS

Wostman, B. S., Ed., Gnotobiotes: Standards and Guidelines The Breeding, Care, and Management of Laboratory Animals, National Research Counsel, National Academy of Sciences, Washington, D.C., (1970).
Pleasants, J. R. et al., Journal Nutrition, Adequacy of Chemically Defined, Water-Soluble Diet for Germfree BALB/C Mice through Successive Generations and Litters 116, 1949-1964 (1986).
Hooijkaas, H. et al., Journal of Immunology, 134,2223-2227 (1985), Frequency Analysis of Functional Immunoglobulan C- and V-Gene Expression by Mitogen Reactive B Cells and Germfree Mice Fed Chemically Defined Ultra-Filtered "Antigen Free" Diet.
Hoojikaas, H. et al., Germfree Research: Microflora Control and its Application to the Biomedical Sciences, 359-362 (1985), Isotype Expression and Specificity Repertoire of Lipopolysaccharide-Reactive B Cells in Germfree Mice Fed Chemically Defined Ultrafiltered Antigen Free Diet.
Suter, M. et al., Infection and Immunity, 49, 615-620 (1985) Stimulation of Immunoglobulin Containing Cells and Isotype-Specific Antibody Response in Experimental *Mycoplasma hyponeumoniae* Infection in Specific Pathogen-Free Pigs.
Umehara, K. et al., Germfree Research: Microflora Control and its Application to the Biomedical Sciences, 351-353 (1985), The Effect of the Antigenic Stimuli Derived from the Diet in Microbial Flora on Immunoglobulin Levels.
Wostmann, B. et al., Ed., Germfree Research Microflora Control and its Applications to the Biomedical Sciences, Allan Liss, Publisher, New York, (1984).
Bos, N. A. et al., Cellular Immunology, 105, 235-245 (1987), Early Development of Ig-Secreting Cells in Young of Germfree BALB/C Mice Fed A Chemically Defined Ultrafiltered diet.
Hooijakaas, H. et al., Germfree Research: Microflora Control and its Application to the Biomedical Sciences, 355-358 (1985), Isotype Distribution and Specificity Repertoire of "Spontaneously" occurring (Background) Immunoglobulin-Secreting Cells and Germfree Mice Fed Chemically Defined Ultrafiltered Antigen-free Diet.
Suzuki, T. et al., Germfree Research: Microflora Control and its Application to the Biomedical sciences, 325-328 (1985), Immunoresponses and Natural Killer Activity of Nude and Normal Mice Under Conventional and Germfree Conditions.

(List continued on next page.)

*Primary Examiner*—David L. Lacey
*Assistant Examiner*—Susan L. Futrovsky
*Attorney, Agent, or Firm*—Pennie & Edmonds

[57] ABSTRACT

The subject invention relates a method for the production of monoclonal antibodies. The method utilizes an immunized antigen free animal. The invention also provides a method for the use of such monoclonal antibodies, and polyclonal antibodies derived from an immunized antigen free animal, for in vitro and in vivo clinical diagnostics and therapeutics. Also, the subject invention provides a fibrin-specific monoclonal antibody.

8 Claims, No Drawings

OTHER PUBLICATIONS

Pleasants, J., C.R.C. Handbook of Immunology in Aging, 257–297, (1981), The Germfree System for Aging and Immunity.

Sasaki, S., Germfree Research: Microflora Control and its Application to the Biomedical Sciences, 9–15 (1985), The Present Status of Clinical Applications of Germfree Technology.

Trexler, P., Germfree Research: Microflora Control and its Application to the Biomedical Sciences, 3–7, (1985), The Evolution of Gnotobiotic Technology.

Gustafsson B., Germfree Research: Microflora Control and its Application to the Biomedical Sciences, 17–23, (1985), The Future of Germfree Research.

Bos, N. A., et al., Cellular Immunology, 112, 371–380 (1988), The Influence of Exogenous Antigenic Stimulation on the Specificity Repertoire of Background Immunoglobulin-Secreting Cells of Different Isotypes.

Stepankova, R. et al., Folia Microbiol., 30, 291–294 (1985), Immunoglobulin-Producing Cells in Lymphatic Tissues of Germfree and Conventional Rabbits as Detected by an Immunofluorescence Method.

Bos, N. A., et al., Journal of Reproductive Immunology, 9, 237–246, "Background" Ig-Secreting Cells in Pregnant Germfree Mice Fed a Chemically Defined Ultrafiltered Diet.

Pleasants, J. R., et al., S. Sasaki et al. (eds), Recent Advances in Germfree Research, pp. 535–538, Tokai University Press (1981), entitled: Immune Response of Germfree C3H Mice Fed Chemically Defined Ultrafiltered "Antigen-Free" Diet.

Olson, G. et al., The Journal of Immunology, 97, 275286 (1966), Cellular and Humoral Immune Response of Germfree Mice Stimulated with 75 HGG or *Salmonella typhimurium*.

Ohwake, M., et al., Immunology, 32, 43–48 (1977) A Comparative Study on the Humoral Immune Response in Germ-free and Conventional Mice.

Umehara, K., et al., S. Sasaki (eds.) Recent Advances in Germfree Research, pp. 453–457, Tokai University Press (1981), Enteric Adenovirus Infection of Germfree Mice Reared on an Antigen-Free Diet.

Coates, M., et al. (Eds.), The Germ-Free Animal in Biomedical Research (1984) London, pp. 335–384.

Underwood et al. Clin. exp. Immunol. 60:417–426 (1985) Hybrids From Normal Germfree, Nude and Neonatal Mice Produce Monoclonal Auto Antiboidies to Eight Different Intracellular Structures.

Köhler, G. and Milstein, C. Eur. J. Immun. 6:511–519 (1976) Derivation of Specific Antibody-Producing Tissue Culture and Tumor Lines by Cell Fusion.

METHOD FOR PRODUCTION OF ANTIBODIES UTILIZING AN ANTIGEN-FREE ANIMAL

This is a continuation of application Ser. No. 364,053, filed Jun. 8, 1989, now U.S. Pat. No. 5,120,834, which is a continuation-in-part of application Ser. No. 206,259, filed Jun. 13, 1988, now abandoned.

FIELD OF THE INVENTION

The subject invention relates a method for the production of monoclonal antibodies. The method utilizes an immunized germfree animal. The invention also provides a method for the use of such monoclonal antibodies, and polyclonal antibodies derived from an immunized germfree animal, for in vitro and in vivo clinical diagnostics and therapeutics. Also, the subject invention provides a fibrin-specific monoclonal antibody.

BACKGROUND OF THE INVENTION

Kohler and Milstein are generally credited with having devised the techniques that successfully resulted in the formation of the first monoclonal antibody-producing hybridomas (G. Kohler and C. Milstein, 1975, Nature 256, 495-497; 1976, Eur. J., Immunol. 6, 511-519). By fusing antibody-forming cells (spleen B-lymphocytes) with myeloma cells (malignant cells of bone marrow primary tumors) they created a hybrid cell line, arising from a single fused cell hybrid (called a hybridoma or clone). The hybridoma had inherited certain characteristics of both the lymphocytes and the myeloma cell lines. Like the lymphocytes, the hybridoma secreted a single type of immunoglobulin; moreover, like the myeloma cells, the hybridoma had the potential for indefinite cell division. The combination of these two features offered distinct advantages over conventional antisera.

Antisera derived from vaccinated animals are variable mixtures of polyclonal antibodies which never can be reproduced identically. Monoclonal antibodies are highly specific immunoglobulins of a single type. The single type of immunoglobulins secreted by a hybridoma is specific to one and only one antigenic determinant, or epitope, on the antigen, a complex molecule having a multiplicity of antigenic determinants. For instance, if the antigen is a protein, an antigenic determinant may be one of the many peptide sequences (generally 6-7 amino acids in length; M. Z. Atassi, 1980, Molec. Cell. Biochem. 32, 21-43) within the entire protein molecule. Hence, monoclonal antibodies raised against a single antigen may be distinct from each other depending on the determinant that induced their formation; but for any given hybridoma, all of the antibodies it produces are identical. Furthermore, the hybridoma cell line is easily propagated in vitro or in vivo, and yields monoclonal antibodies in extremely high concentration.

A monoclonal antibody can be utilized as a probe to detect its antigen. Thus, monoclonal antibodies have been used in in vitro diagnostics, for example, radioimmunoassays and enzyme-linked immunoassays (ELISA), and in in vivo diagnostics, e.g. in vivo imaging with a radiolabeled monoclonal antibody. Also, a monoclonal antibody can be utilized as a vehicle for drug delivery to such antibodies, antigen.

However, before a monoclonal antibody can be utilized for such purpose, it is essential that the monoclonal antibody be capable of binding to the antigen of interest; i.e., the target antigen. This procedure is carried out by screening the hybridomas that are formed to determine which hybridomas, if any, produce a monoclonal antibody that is capable of binding to the target antigen. This screening procedure can be very tedious in that numerous, for example, perhaps several thousand, monoclonal antibodies may have to be screened before a hybridoma that produces an antibody that is capable of binding the target antigen is identified. Accordingly, there is the need for a method for the production of monoclonal antibodies that increases the likelihood that the hybridoma will produce an antibody to the target antigen.

SUMMARY OF THE INVENTION

The subject invention provides a method for the production of monoclonal antibodies to an antigen comprising:
(a) immunizing a germfree animal with said antigen to permit antibody-producing cells to produce antibodies to said antigen,
(b) removing at least a portion of said antibody-producing cells from said germfree animal,
(c) forming a hybridoma by fusing one of said antibody-producing cells with an immortalizing cell wherein said hybridoma is capable of producing a monoclonal antibody to said antigen,
(d) propagating said hybridoma, and
(e) harvesting the monoclonal antibodies produced by said hybridoma.

The subject invention also provides methods for utilizing a monoclonal antibody or a polyclonal antibody derived from a germfree animal. The subject invention also provides a fibrin-specific monoclonal antibody and methods for utilizing such a monoclonal antibody.

DETAILED DESCRIPTION OF THE INVENTION

THE GERMFREE ANIMAL

The subject invention relates to the use of a germfree animal for the production of monoclonal antibodies. Germfree animals were first developed in the latter part of the 19th century and have been utilized extensively since such time.

A germfree animal is a gnotobiote that is free from all demonstrable associated forms of life, including bacteria, viruses, fungi, protozoa, and other saprophytic or parasitic forms. A gnotobiote is an animal or strain derived by aseptic cesarean section or sterile hatching of eggs that is reared and continuously maintained with germfree techniques under isolator conditions and in which the composition of any associated fauna and flora, if present, is fully defined by accepted current methodology. (It should be noted that all mice carry a latent leukemogenic virus and, therefore, a mouse that would be germfree but for such leukemogenic virus shall be considered a germfree animal for the purpose of the subject invention.)

The essence of a germfree system is the provision of barriers against the entry of unwanted microbial invaders. In addition to the physical barriers of plastic, metal, rubber and glass which enclose the animals, the system requires the operational barriers of air filtration, food and water sterilization, manipulation by gloves, which form an integral part of the barrier system. Also, the entry of supplies to the isolator should be performed under sterile conditions.

It is believed that any germfree animal can be utilized in the subject invention. The most common germfree animals are mouse, pig, rat, rabbit, guinea pig, goat, sheep, primate and poultry with a mouse being preferred, especially a Balb/C mouse.

PRODUCTION, CARE AND MAINTENANCE OF GERMFREE ANIMALS

There have been numerous publications concerning the production, care and maintenance of germfree animals. For example, Wostmann, B. S., Ed., Gnotobiotes: Standards and Guidelines for the Breeding, Care and Management of Laboratory Animals, National Research Council, National Academy of Sciences, Washington, D.C. 1970; Coates, M. E., et al., The Germfree Animal in Research, Academic Press, London, 1968; and Pleasants, J. R., Gnotobiotics, in Handbook of Laboratory Animal Science, Vol., 1, Melby, E. C., et al., Eds., CRC Press, Boca Raton, Fla., 117, (1974) the disclosure of which is incorporated herein by reference.

What follows is a summary derived from the article Wostmann, B. S. ed., (1970) Gnotobiotes Standards and Guidelines for the Breeding, Care and Management of Laboratory Animals, National Research Council, National Academy of Sciences, Washington, D.C. describing the production, care and maintenance of germfree rats and mice. It should be noted that such production, care and maintenance is similar for other animals.

ROOM ENVIRONMENT

The facilities, equipment, and husbandry procedures shall be designed and operated so as to afford maximum environmental control and optimal comfort and welfare for the animals. The cages, feeders and waterers shall be so designed and fabricated as to afford maximum comfort for the animals, to make the food and water readily available, and to make cleaning and sterilization practicable and efficient.

A desirable floor plan for extensive germfree work should consist of:

1. a work area for assembling and sterilizing the isolators,
2. an area for maintaining the isolators with animals, and
3. a laboratory area for the routine monitoring of the gnotobiotic environment.

An office and diet-preparation area may be incorporated in the floor plan.

The room environment for maintaining gnotobiotic isolators should meet the standards established for housing conventional laboratory rodents. The structure should be insect-proof, and the walls and floor should be moistureproof. Lighting should be uniform, with the same light-dark cycle throughout the year. Ventilation should rapidly remove any fumes caused by chemical sterilization, and the climate should be controlled as specified below.

Temperature. The generally accepted animal room temperature of 21°-27° C.(70°-80° F.) may need to be adjusted downward to keep the isolator temperature between 22° and 26° C. (72° and 78° F.).

Humidity. The relative humidity (RH) should be kept at the human comfort level of 40-60 percent. However, when room air is used to ventilate the isolator, 40-50 percent RH is recommended.

Ventilation. The room-air changes should be sufficient to remove rapidly any fumes generated during chemical sterilization. Ten to fifteen air changes per hour are recommended. Head masks with fresh-air ventilation should be available to protect personnel exposed to dangerous levels of chemical fumes.

*GERMFREE EQUIPMENT* (See Sacquiet, E. 1968, Equipment design and management: General technique of maintaining germ-free animals, p. 1-22 In M. E. Coates [ed]. the germfree animal in research. Academic Press, London; Trexler, P. C. 1968. Equipment design and management: Transport of germ-free animals and current developments in equipment design, p. 23-35 In M. E. Coates [ed]. The germfree animal in research. Academic Press, London)

Complete exclusion of environmental microbes requires an absolute barrier. The successful operation of the isolator depends on the maintenance of that barrier at all times. There are two general types of isolators available, metal and plastic. Some metal units are built to withstand internal steam pressure of 20 psi (1,406 g/cm$^2$). (See Reyniers, J. A. 1959. Design and operation of apparatus for rearing germ-free animals. Ann. N.Y. Acad. Sci. 78:47; Miyakawa, M. 1959. The Miyakawa remote-control germfree rearing unit. Ann. N.Y. Acad. Sci. 78:37). Others are generally placed in a large autoclave for initial sterilization (See Gustafsson, B. E. 1959. Lightweight stainless steel systems for rearing germ-free animals. Ann. N.Y. Acad. Sci. 78:17.).

The flexible-film isolator (See Trexler, P. C., and L. I. Reynolds. 1957. Flexible film apparatus for the rearing and use of germfree animals. Appl. Microbiol. 5:406) is now the most widely used unit. It is usually made of flexible laminated vinyl, must be chemically sterilized, and is readily adapted to specific needs. Another type, made from a large tube of nylon, tied at each end, can be sterilized in an autoclave. (See Lev, M. 1962. An autoclavable plastic unit for rearing animals under germfree conditions. J. Appl. Bacteriol 25:30). Plexiglass isolators and disposable flexible-film units also have been developed. Many of these are light enough to be stacked two or three high on a rack, a feature that conserves floor space.

A special cylinder for sterilizing food and supplies is generally used with the heat-sensitive isolators. It should be designed with a large filtration area to facilitate air removal in a high-vacuum autoclave (See Trexler, P. C. 1963. An isolator system for control of contamination. Lab. Anim. Care. 13:572). Alternatively, the cylinder may be fitted with a drain tube vented to the atmosphere for removal of air and condensation during sterilization without the benefit of a vacuum. (See Jaworski, N. E., and C. E. Miller. 1963. Refinement of the cylinder technique for supplying germfree isolators. Lab. Anim. Care. 13:591).

STERILIZATION

All equipment, food, bedding, water, and air used in the isolator must be absolutely sterile. The methods and conditions employed are determined by characteristics of the individual items.

Steam under pressure is the best-known method of sterilization. It is particularly suitable for porous items that are heat-stable. Every area that can conceivable harbor microbes must be brought into direct contact with steam. Exposure time is related to the temperature used. It is recommended that the least accessible portion of the load (the center of the packages) be exposed for a minimum period of 15 minutes at 121° C. (250° F.). Higher temperatures and shorter exposure periods may be used after careful testing to ensure sterility. Standard package size and density of diet, bedding, and other materials are of primary importance to assure that the steam penetration time will be constant and predictable.

Dry heat has been used for sterilization of the air supply for the isolator (See Miyakawa, M. 1959. The Miyakawa remote-control germfree rearing unit. Ann. N.Y. Acad. Sci. 78:37; Gustafsson, B. E. 1959. Lightweight stainless steel systems for rearing germ-free animals. Ann. N.Y. Acad. Sci. 78:17).

Peracetic acid ($CH_3COOOH$) is widely used on heat-sensitive, non-porous materials, especially the flexible-film units. This acid is used in a 2 percent solution with a wetting agent (detergent) (See Trexler, P. C., and L. I. Reynolds. 1957. Flexible film apparatus for the rearing and use of germfree animals. Appl. Microbiol. 5:406). Other chemicals can be used for special situations, e.g., hypochlorites, iodophors, or quarternary ammonium compounds in the liquid trap to introduce newborns obtained by hysterectomy, or $HgCl_2$ to introduce eggs under sterile conditions prior to hatching.

Ethylene oxide (ETO) may be used to sterilize non-wettable heat-sensitive items. Sterilization time is dependent on the temperature, humidity, pressure, and concentration of ETO. ETO may react chemically with bedding and dietary components to produce toxic or undesirable compounds. Because of its flammability and toxic hazards, routine use of ETO for sterilization should be restricted to the commercially available gas mixtures, which contain not more than 20 percent ETO.

Fiberglass filters are commonly used for sterilization of the air supply. They should function as absolute filters.

Membrane filtration of liquids can be used to avoid exposure to heat, provided these membranes are absolute filters, for example, a filter that excludes particles greater than 0.2 micrometers in diameter.

Irradiation by gamma rays or electron-beam sources may be used to sterilize diets or other special items. Dosages employed vary from 2.5 to $6 \times 10^6$ rads.

INTERNAL ENVIRONMENT

Temperature. The internal isolator temperature is a function of the room environment and should be maintained between 22° and 26° C. (72°-78° F.).

Humidity. The isolator is subject to condensation of moisture in cases of overloading, inadequate ventilation, or both. Air entering the isolator should be below 50 percent RH and preferably above 40 percent RH.

Air Supply. The isolator should have 12 to 20 air changes per hour and a positive pressure of 3-5 in. (8-13 cm) of water. Air may be supplied from a central source or from individual blowers for each unit. A turbine-type air compressor is recommended for a central air supply system because the oil piston type tends to atomize oil into the air-supply lines.

An air diffusion isolator (See Trexler, P. C. 1968. Equipment design and management: Transport of germ-free animals and current developments in equipment design, p. 23-35 In M. E. Coates [ed]. The germfree animal in research. Academic Press, London) is not subject to loss of ventilation in the event of power failure. However, this type has the disadvantage of fewer air changes per hour and lacks the protective positive pressure that could help prevent contamination should small breaks occur in the barrier.

Emergency Safeguards. Adequate provisions for the maintenance of air pressure within the isolator in the event of power failure or mechanical failure must be provided with not more than a few minutes, interruption in the air supply. Collapse of unsupported film isolators may eventually result in suffocation of the animals, but the more immediate danger is that the animals may be able to reach and damage film or gloves. This may be prevented temporarily by plugging air conduits with rubber stoppers. The operation of individual isolator air supplies requires only an emergency power supply. A central air system should have a second turbine compressor for standby air supply.

Graphic recording of the temperature and pressure is recommended. An audiovisual alarm system should be incorporated in a central air system to be actuated by a drop in line pressure in the event of either loss of power or mechanical failure. Similar alarm systems should indicate undesirable fluctuations in the temperature of the air supply. For individual isolator air systems, continuous graphic monitoring of the room environment is recommended.

CAGING AND INTERIOR EQUIPMENT

Equipment. A basic list of equipment for an isolator may include cages with secure lids, water bottles and food hoppers, protective cloth gloves for the rubber gloves, an extra door gasket or cap closing ring, long rubber-tipped forceps, hemostats, scissors, a towel, gauze sponges, a two-quart can for holding instruments, a covered four-quart diet can, spoon, culture tubes, paper bags, and moisture-resistant bags for dirty bedding.

Cages should be fabricated of a smooth corrosion-resistant material. They should be impervious to liquids and easily sterilized. Materials considered acceptable include plastics, stainless steel, and glass. Galvanized metal becomes corroded and is not recommended because trace-metal contamination may influence experimental results.

Cage dimensions are usually limited by the size of the entry port. The minimum area for a female mouse and litter is 50 in.$^2$ (970cm$^2$). In many circumstances more space per animal may be needed.

Table 1 lists the recommended floor space per animal for mice and rats according to weight groupings.

TABLE 1

Amount of Floor Space Recommended per Animal for Caged Mice and Rats

| Category Number | Weight (g) | Space per Animal in.$^2$ (cm$^2$) | Maximum Population Per Cage |
|---|---|---|---|
| MICE | | | |
| 1 | up to 10 | 6 (40) | 40 |
| 2 | 10-15 | 8 (50) | 30 |
| 3 | 15-25 | 12 (75) | 20 |
| 4 | over 25 | 15 (95) | 16 |
| RATS | | | |
| 1 | up to 50 | 15 (95) | 50 |
| 2 | 50-100 | 17 (110) | 50 |
| 3 | 100-150 | 19 (125) | 40 |
| 4 | 150-200 | 23 (150) | 40 |
| 5 | 200-300 | 29 (185) | 30 |
| 6 | over 300 | 40 (260) | 25 |

MISCELLANEOUS RECOMMENDATIONS

Freon tests for minute leaks are recommended to ensure the integrity of the barrier system.

Each unit should be equipped with its own operation log to maintain a chronological record of every procedure involving the unit from the time it is assembled and sterilized. Such records are conveniently kept in metal hospital-chart holders identified by the isolator number. They should also contain notes for routine maintenance, e.g., glove replacement. Breeding-performance records may be kept in the same chart holder.

Due to the limited space available inside the isolators, paper and folding containers are recommended for diets and bedding, and for the transport of animals between isolators linked by a sterile passage.

No ether should be used inside an isolator because it may explode when static sparks occur. Fluothane (bromochlorotrifluoroethane) is recommended as a volatile, nonflammable anesthetic.

DIETS, BEDDING AND WATER
GENERAL RECOMMENDATIONS

The complete formula for commercially produced diets should be provided, listing all the ingredients and their concentrations, including preservatives, antioxidants, and other additions. The date of production should be clearly indicated. The manufacturer should guarantee that the diet is:

1. Within the normal acceptable limits of naturally occurring hormone activity.
2. Free of additives containing drugs, hormones, antibiotics, or any other substance that may create abnormal physiological conditions or interfere with investigative procedures.
3. Free of salmonella on the basis of statistically selected samples.
4. Free of rodent and vermin contamination.
5. Free of all unrendered meat scraps or fish meal that may contain pathogens.

FORTIFICATION OF DIETS

Diets of germfree animals must contain more than normal requirements of certain nutrients to compensate for the heat-sterilization loss of vitamins (especially certain B vitamins and vitamins A and D) and of the nutritive value of protein (reduction in available lysine, methionine, arginine and tryptophan). They must also provide required nutrients, which in conventional animals would be available through microbial synthesis in the gastrointestinal tract (See Reddy, B. S., B. S. Wostmann, and J. R. Pleasants. 1968 Nutritionally adequate diets for germ-free animals, p. 87–111 In M. E. Coates [ed].. the germ-free animal in research. Academic Press, London). An example of such a diet is L-485, an inexpensive diet that has been extensively tested (See Kellogg, T. F., and B. S. Wostmann. 1969. Rat and mouse stock diet L-485. Lab. Anim. Care.) and can be commercially produced (see Table 2). Supplementation with specific amino acids rather than increased total protein content should be considered as a means to compensate for loss in protein quality. Increasing the total protein content of the diet will result in a greater consumption and excretion of water, causing humid conditions and thereby limiting the number of animals that can be housed in an isolater of a given size.

TABLE 2

| Composition of Diet L-485 for Rats and Mice | |
|---|---|
| Ingredient | Amount per kg |
| DIET | |
| Ground yellow corn (maize) | 590 g |
| Soybean oil meal (crude protein 50 percent) | 300 |
| Alfalfa meal (dehydrated; 17 percent protein) | 35 |
| Corn oil (once refined) | 30 |

TABLE 2-continued

| Composition of Diet L-485 for Rats and Mice | |
|---|---|
| Ingredient | Amount per kg |
| NaCl | 10 |
| CaHPO$_4$ 2H$_2$O | 10 |
| CaCO$_3$ | 5 |
| Lysine (feed grade) | 5 |
| Methionine (feed grade) | 5 |
| B.H.T. (butylated hydroxytoluene) | 0.125 |
| Trace mineral mix | 0.25 |
| VITAMIN MIX | |
| A | 26,000 IU |
| D$_3$ | 1,000 IU |
| E (a tocopherol acetate) | 225 mg |
| K$_3$ (menadione) | 90 |
| Riboflavin | 30 |
| Pantothenic acid | 285 |
| Niacin | 65 |
| Choline chloride | 2,000 |
| B$_{12}$ (0.1 percent trituration in mannitol) | 2 |
| Thiamine HCl | 65 |
| Pyridoxine HCl | 20 |
| Folic acid | 10 |
| Para-aminobenzoic acid | 50 |
| TRACE MINERAL MIX (commercial) | |
| MN as manganous oxide | 65 mg |
| Fe as ferrous carbonate | 20 |
| Cu as copper oxides | 2 |
| Zn as zinc oxide | 15 |
| I as calcium iodate | 1.5 |
| Co as cobalt carbonate | 0.6 |

Steam sterilization (See Reddy, B. S., B. S. Wostmann, and J. R. Pleasants. 1968 Nutritionally adequate diets for germ-free animals, p. 87–111 In M. E. Coates [ed]. the germ-free animal in research. Academic Press, London)

Actual procedures will depend on the equipment available. Three factors are of general importance:

1. A pre-sterilization vacuum, whenever possible, of at least 20 in. Hg will assist steam penetration of the diet in a clave or cylinder vented to the atmosphere. A vacuum of 28 in. Hg or more is recommended when the supply cylinder is not vented to the atmosphere.
2. Use of the shortest sterilization phase that will ensure total sterility, with an added safety margin dictated by equipment and skill. Temperatures measured at the inner core of the diet should reach at least 121~C. (250~F.). At that temperature the actual sterilization phase should last a minimum of 15 minutes. With higher sterilization temperatures, sterilization times will be relatively shorter.
3. A post-sterilization vacuum will speed the reduction of temperature of the diet. This will avoid unnecessary heat destruction of nutrients. However, the design and performance of the apparatus must be adequate to avoid leaks during this stage of the operation.

In steam sterilization of diets, the goal is to avoid both incomplete sterilization and unnecessary nutritional damage caused by excessively prolonged heating. Although some nutrient loss is unavoidable, quite acceptable results may be obtained by manipulation of:

(a) Technical procedures such as temperature, time pre-sterilization and post-sterilization vacuum, and pellet size.

(b) The water content of the diet. An increase in water content leads to better recovery of B vitamins after sterilization (See Zimmerman, D. R., and B. S. Wostmann. 1963. Vitamin stability in diets sterilized for germfree animals. J. Nutr. 79:318). For solid diets, a water content up to 25 percent, or as high as proves to be compatible with the storage quality of the diet, is recommended. A change in water content of the diet should be followed by a new test of the rate at which the diet reaches sterilizing temperature. RADIATION STERILIZATION (See Reddy, B. S., B. S. Wostmann, and J. R. Pleasants. 1968. Nutritionally adequate diets for germfree animals, p. 87-111 In M. E. Coates [ed]. The germ-free animal in research. Academic Press, London; Ley, F. J., J. Bleby, M. E. Coates, and J. S. Paterson. 1969. Sterilization of laboratory animal diets using gamma radiation. Lab. Anim. 3:221)

Techniques and dosimetry will depend on equipment and type of radiation. Although, in general, radiation sterilization is considered to result in less destruction of nutrients, it is at present recommended that diets be sterilized with steam.

TEST FOR STERILITY

To monitor sterility achieved with any specific sterilization procedure, the use of *Bacillus stearothermophilus* spore strips is recommended. The strips should be embedded in the core of the diet. Also, the isolator and its animals should be periodically microbiologically monitored. Such monitoring is necessary to test for accidental contaminations resulting from breaks in the isolator barriers or from inadequate sterilization of the isolator or its contents. This can be accomplished as described in Wostmann, B. S., Ed., Gnotobiotes: Standards and Guidelines for the Breeding Care and Management of Laboratory Animals, National Research Council, National Academy of Sciences, Washington, D.C., 1970, pp. 28-39.

ESTIMATION OF NUTRIENT LOSS DURING STERILIZATION

As a useful check on the loss of vital nutrients, determination of acid-extractable thiamine as an indicator of the recovery of thiamine added to the diet is recommended (See Wostmann, B. S. and P. L. Knight. 1960. The effect of methyl alcohol on the conversion of thiamine to thiochrome. Experientia 16:500). A recovery of less than 25 percent indicates severe impairment of general nutritional quality of the diet. With adequate equipment and care, recoveries of 50 percent or more should be achieved.

STORAGE OF SOLID DIET

Because of the generally high cost of germfree experimentation, extra care should be taken never to use diet that has decreased significantly in nutritional value. It is recommended that (a) nonsterilized diet always be stored under refrigeration, and never for longer than one month, and that (b) storage time of sterilized diet inside the isolator should be one week or less and must never exceed ten days.

BEDDING

Bedding should be changed at least once a week. It is recommended that bedding material be easy to sterilize and not readily eaten by the animals. It should not yield toxic compounds as a result of the sterilization procedure. Dustfree white pine chips (sawdust) and shavings are recommended. Basswood and poplar shavings or crushed corn cobs are acceptable. Diatomaceous products, cedar, resinous woods, and hardwoods are not recommended. Ethylene oxide sterilization should not be used until the question of possible formation of harmful compounds has been clarified.

WATER

Drinking water must be sterilized. It may be autoclaved in square pack flasks, Mason jars, or tanks attached to the unit. A small air space should be left inside each container.

PRINCIPLES OF CESAREAN DERIVATION OF GNOTOBIOTES

The success of any cesarean operation is keyed in part to having the pregnancy advance to full term. This is particularly true of animals with short gestation periods, where the fetus may gain 20 percent of its weight in the final 24 hours before parturition. Timed matings are reasonably successful, but with animals yielding large litters (rats and mice) it may be helpful to wait for the female to deliver the first offspring before proceeding with the operation. In guinea pigs, the most satisfactory method is to select females for surgery by measuring the spread of the pubic bones (See Philips, B. P., P. A. Wolfe, and H. A. Gordon. 1959. Studies on rearing the guinea pig germfree. Ann. N.Y. Acad. Sci. 78:183).

The cesarean-derived young must be delivered into a germfree environment before they take their first breath of air. They may be taken directly from the mother by hysterotomy, through an incised sterile barrier membrane into a sterile isolator, or by hysterectomy, through a germicidal trap into a sterile isolator. The usual surgical preparation of the female prior to the cesarean operation includes removal of abdominal hair and cleaning and disinfection of the operative site. Anesthesia is accomplished preferentially by dislocation of the cervical vertebrae in rats and mice, although an abdominal midline local anesthetic or general anesthesia may also be used without incurring serious levels of fetal depression and mortality. With guinea pigs, surgery is generally performed after prior sedation and under local anesthesia.

Delivery of the young by hysterotomy through a barrier membrane requires special isolator equipment. The Reyniers stainless-steel surgical unit (See Reyniers, J. A. 1965. Germfree life methodology (gnotobiotics) and experimental nutrition. p. 458-466 In Proc. 3rd Internat. Congr. Biochem., Bruxelles) has a built-in horizontal metal divider that separates the upper and lower compartments of the unit. The divider contains a circular port covered with a mylar plastic film to maintain the integrity of the upper compartment. The female, prepared for surgery, is placed in the lower compartment with the abdomen pressed against the mylar. All surgical instruments are in the upper compartment, and the surgery is performed in this sterile area. An incision is made through the plastic and skin with an electrocautery or scalpel. The self-sterilizing electrocautery blade is preferred for skin incision. The edges of the skin and mylar are clamped together and reflected. A sterile drape is placed over the abdomen to cover the cut edges of the skin, and warm disinfectant (benzalkonium chloride 1:1,000) is applied to the exposed fascia before opening the abdominal cavity. Extreme caution must be exercised to avoid cutting into the bowel. The insertion of a pair of forceps or hemostats between the peritoneal wall and the viscera may be helpful. The uterus is then opened and the young removed. The fetal membranes are removed, and the umbilical cord is clamped and cut. The young are gently dried and massaged to stimulate respiration. They are then transferred to a rearing unit to be fosternursed or hand-fed. Another sheet of mylar may be secured over the surgical port and the procedure repeated with as many as 5 or 6 females without serious risk of contamination. Cesarean delivery may also be accomplished using a plastic isolator or glove bag as a surgical unit. The exterior surface of the isolator floor is presterilized and brought into contact with the animal's abdomen, thus serving the same purpose as the mylar sheet described above. Following the operation the slit in the plastic barrier can be closed with sterile tape and the surgical procedure repeated on additional gravid females.

Delivery of the young by hysterotomy is more common when plastic isolators are used (See Foster, H. 1959. A procedure for obtaining nucleus stock for a pathogen-free animal colony. Lab. Anim. Care 9:135). The uterus is aseptically exposed and clamped just anterior to the cervix. The excised uterus is transferred into the germfree unit through a liquid germicidal trap. Once inside the isolator, the young are delivered as rapidly as possible to prevent aspiration of fetal fluids. Normally they are dried and breathing well before the umbilical cord is clamped and cut. The infants are then given to the foster mother or hand reared.

Hysterotomy may be used successfully for mice, rats, and swine. In guinea pigs, however, hysterotomy is preferred, since a high mortality occurs if as much as two minutes elapses between the severance from the maternal blood supply and delivery inside the isolator.

BREEDING SYSTEMS IN GNOTOBIOTIC COLONIES

INBRED STRAINS

The usual brother X sister mating system employed in conventional breeding colonies can also be used in gnotobiotic colonies.

NONINBRED STOCKS

True random breeding includes some matings of siblings and of first cousins. Although such matings are normally avoided in noninbred breeding colonies, the resulting mating system does not decrease the rate of inbreeding to the maximum extent possible. Any system of minimal inbreeding can be used. (See Falconer, D.C. 1967. Genetic aspects of breeding methods. p. 72-96 In The UFAQ handbook on the care and management of laboratory animals, 3rd ed. E and S Livingstone, LTd., London; National Research Council, Institute for Laboratory Animal Resources. 1969. A guide to genetic standards for laboratory animals. National Academy of Sciences, Washinton, D.C.).

Comparable Conventional and Gnotobiotic Colonies. If it is desired to maintain both conventional and gnotobiotic colonies for comparative purposes, their similar genetic constitutions may be maintained by introducing cesarean-derived litters from the effective breeding population of the conventional colony into the gnotobiotic colony. This appears to be the method of choice for those producers who place most emphasis on the production of nongnotobiotic rats and mice but has the disadvantage of preventing the establishment of a microbiological pedigree that would simplify microbiological monitoring. Ideally, this could be done by using litters from specific matings as breeding stock for the conventional colony and using the next litter from each of these matings as breeding stock for the gnotiobiotic colony. If this procedure is followed every second or third generation, the genetic constitutions of both colonies should remain very similar, provided, of course, that the same mating system is used in each colony.

Alternatively, litters from the effective breeding population of the gnotobiotic colony may be used to establish or replenish the conventional colony. The genetic consequences will be identical, provided the same procedures are followed.

*RECORD-KEEPING* (See Wolff, G. L. 1967. Practical mating systems and record-keeping in a breeding colony. p. 97-113 In the UFAW handbook on the care and management of laboratory animals, 3rd ed. E. and S Livingstone, Ltd., London).

Proper records should be kept for the animals and for the maintenance of the isolator. The animals' records should determine the efficiency of the operation and the biological performance of the animals. The isolator records should maintain a chronology of events related to the isolator to assist in locating a breach of the barrier if contamination occurs.

THE ANTIGEN-FREE ANIMAL

In a preferred embodiment of the subject invention, it is preferred that the germfree animal be bred on a chemically defined (CD), low molecular weight, water-soluble, ultrafiltered diet. It is believed that such a diet permits one to obtain complete control of nutrient and antigen intake by the animal. Such a diet is generally made up entirely of ingredients that are capable of chemical definition, e.g., amino acids, simple sugars, lipids, vitamins and minerals. For the purpose of the subject invention a chemically defined diet comprises amino acids, simple sugars, lipids, vitamins and minerals and no other component having a molecular weight greater than about 10,000 daltons. Thus, all of the components of a CD diet are of low molecular weight and are naturally circulating nutrients in animals and, therefore, it is believed that such components will not stimulate an immune response. The recent literature refers to a germfree animal that has been bred on a CD diet as an "antigen-free animal".

Also, it is preferred to utilize a filter paper bedding, otherwise the germfree animal may eat the bedding, which results in an immune response. It is believed that the eating of a filter paper bedding does not result in an immune response.

The particular CD diet for a given species would use such components in proportions and quantities so as to fulfill known nutritional requirements for such species. The composition and preparation of a preferred CD diet for germfree mice is as follows:

| Composition and preparation of chemically defined diet L489E14Se | |
|---|---|
| Ingredient | Amount (grams/100 grams of Ingredient) |
| To 192 ml Milli-Q water at 70~C. the following are added: | |
| Leucine | 1.9 |
| Phenylalanine | 0.74 |
| Isoleucine | 1.08 |
| Methionine | 1.06 |
| Tryptophan | 0.37 |
| Valine | 1.23 |
| Asparagine | 0.91 |
| Arginine HCl | 0.81 |
| Threonine | 0.74 |
| Lysine HCl | 1.77 |
| Histidine HCl | 0.74 |

-continued

Composition and preparation of chemically defined diet L489E14Se

| Ingredient | Amount (grams/100 grams of Ingredient) |
|---|---|
| The solution is cooled to 45~C. and the following added: | |
| Glycine | 0.59 |
| Proline | 1.48 |
| Serine | 1.33 |
| Alanine | 0.59 |
| Sodium glutamate | 3.40 |
| L-tyrosine ethyl ester HCl | 0.62 |
| Ferrous gluconate | 0.05 |
| Salts 35D[1] | 0.105 |
| Sodium Selenite[2] | 0.074 |
| Solution cooled to 5~C. and the following added: | |
| Calcium glycerophosphate | 5.22 |
| Magnesium glycerophosphate | 1.43 |
| Calcium chloride 2H$_2$O | 0.185 |
| Sodium chloride - Potassium Iodide (KI) mix (containing 680 mg KI) | 0.086 0.086 |
| Vitamin B mix 111E5[3] | 0.09 |
| Vitamin B12[4] | 1.20 mg |
| Choline chloride | 0.31 |
| Potassium acetate | 1.85 |
| To 108 ml Milli-Q water at 70~C. | |
| D-Dextrose, anhydrous was added | 71.28 |
| Solutions cooled to 5~C. and combined both for ultrafiltration. | |

[1]Composition of salts 35D mixture given in table 3
[2]Added in addition to sodium selenate in Salts 35D
[3]Composition of vitamin B mix 111E5 as stated in Table 4
[4]Added in addition to vitamin B-12 in vitamin B mix 111E5 (see EXAMPLE hereinbelow)

Such composition is fed to mice or rats ad libitum.

Composition of lipid supplement LADEK 69E6

| Ingredient | Amount per daily adult dose* (0.385 ml) |
|---|---|
| Purified soy triglycerides[1] | 0.33 g |
| Retinyl palmitate | 6.45 mg (11.7 I.U.) |
| Cholecalciferol | 0.0288 mg (1.15 I.U.) |
| 2 ambo-alpha-tocopherol | 3.3 mg |
| 2 ambo-alpha-tocopherol acetate | 6.6 mg |
| Phylloquinone | 72 mg |

*Lactating mice receive twice the normal adult dose.
[1]Consisting of: 12% palmitate
1.5% stearate
24% oleate
55% linoleate
8% linolenate For a detailed description of CD diets see Pleasants, J. R., et al., *J. Nutr.* 116, 1949-1964 (1986), Pleasants, J., et al., *Germfree Research: Microflora Control and Its Application to the Biomedical Sciences*, B. S. Wostmann, Ed., p. 87, Liss, New York (1985); Wostmann, B. S., et al., *J. Nutr.*, 112, 552 (1982); and Pleasants, J. R., et al., *J. Nutr.*, 100, 498 (1970), the disclosures of which are incorporated herein by reference.

PRODUCTION OF MONOCLONAL ANTIBODY

The germfree animal is then utilized for the production of monoclonal antibodies. The germfree system can be utilized to produce a monoclonal antibody to any antigen that the animal in a nongermfree state could produce. As exemplary list of antigens appears in U.S. Pat. No. 3,935,074. However, it is believed that the germfree animal provides a much enhanced immune response to the antigen. Thus, one can increase the likelihood of locating a B-lymphocyte that produces an antibody that is capable of binding to a specific epitope of the antigen. This is a major advantage of the subject invention. In addition, it is believed that the germfree system is particularly useful for generating a highly specific antibody for those antigens with numerous epitopes.

The germfree animal can be immunized by standard techniques. However, it is preferred that the germfree animal be immunized at least three times with at least about three weeks between each immunization, followed by a prefusion booster. It is believed that this increased level of immunization may be necessary because it has been observed that after two immunizations, which is customary, there are still mostly IgM secreting B-lymphocytes rather than the preferred IgG secreting B-lymphocytes.

SOMATIC CELLS

Somatic cells of the germfree animal having the potential for producing antibody and, in particular B lymphocytes, are suitable for fusion with a B-cell myeloma line. Those antibody-producing cells that are in the dividing plasmablast stage fuse preferentially. Somatic cells can be derived from the lymph nodes, spleens and peripheral blood of primed germfree animals, and the lymphatic cells of choice depend to a large extent on their empirical usefulness in the particular fusion system. However, somatic cells derived from the spleen are generally preferred. Once primed or hyperimmunized, germfree animals can be used as a source of antibody-producing lymphocytes. Mouse lymphocytes give a higher percentage of stable fusions with the mouse myeloma lines described hereinbelow. However, the use of antibody-producing cells from other germfree animals is also possible. The choice of a particular germfree animal depends on the choice of antigen, for it is essential that the germfree animal have a B-lymphocyte in its repertoire of B-lymphocytes that can produce an antibody to such antigen.

IMMORTALIZING CELLS

Specialized myeloma cell lines have been developed from lymphocyte tumors for use in hybridoma-producing fusion procedures (G. Kohler and C. Milstein, 1976, Eur. J. Immunol. 6:511-519; M. Schulman et al., 1978, Nature 276:269-270). The cell lines have been developed for at least three reasons. The first reason is to facilitate the selection of fused myeloma cells. Usually, this is accomplished by using myelomas with enzyme deficiencies that render them incapable of growing in certain selective media that support the growth of hybridomas. The second reason arises from the inherent ability of lymphocyte tumor cells to produce their own antibodies. The purpose of using monoclonal techniques is to obtain immortal fused hybrid cell lines that produce the desired single specific antibody genetically directed by the somatic cell component of the hybridoma. To eliminate the production of tumor cell antibodies by the hybridomas, myeloma cell lines incapable of producing light or heavy immunoglobulin chains or those deficient in antibody secretion mechanisms are used. A third reason for selection of these cell lines is their suitability and efficiency for fusion.

Several myeloma cell lines can be used for the production of fused cell hybrids, including NS-1, X63-Ag8, NIS-Ag4/1, MPC11-45.6TG1.7, X63-Ag8.653, Sp2/O-Agf14, FO, and S194/5XXO.Bu.1., all derived from mice, and 210-.RCY3.Agl.2.3 derived from rats. (G. J. Hammerling, U. Hammerling and J. F. Kearnly, eds., 1981, Monoclonal antibodies and hybridomas In J. L. Turk, eds. Research Monographs in Immunology, Vol. 3, Elsevier/North Holland Biomedical Press, New York).

FUSION

Methods for generating hybrids of antibody-producing spleen or lymph node cells and immortalizing cells generally comprise mixing somatic cells with immortalizing cells in a proportion which can vary from about 20:1 to about 1:1 in the presence of an agent or agents (chemical, viral or electrical) that promote the fusion of cell membranes. It is often preferred that the same species of animal serve as the source of the somatic and immortalizing cells used in the fusion procedure. Fusion methods have been described by Kohler and Milstein (1975, Nature 256:495-497; 1976, Eur. J. Immunol. 6:511-519), by Gefter et al. (1977, Somatic Cell Genet. 3:231-236) and by Kozbor et al., 1983, Immunology Today, 4, 72. The fusion-promoting agents used by those investigators were Sendai virus and polyethylene glycol (PEG), respectively.

One can also utilize the recently developed EBV-transformation technique (Cole et al., 1985, Monoclonal Antibodies and Cancer Therapy, Alan R. Liss, Inc., pp. 77-96).

ISOLATION OF CLONES AND ANTIBODY DETECTION

Fusion procedures usually produce viable hybrids at very low frequency, about $1 \times 10^{-6}$ to $1 \times 10^{-8}$. Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium, which contains hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells can synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT media are hybrids formed from myeloma and spleen cells.

To facilitate screening of antibody secreted by the hybrids and to prevent individual hybrids from overgrowing others, the mixture of fused myeloma and B-lymphocytes is diluted in HAT medium and cultured in multiple wells of microtiter plates. In two to three weeks, when hybrid clones become visible microscopically, the supernatant fluid of the individual wells containing hybrid clones is assayed for specific antibody production.

The assay must be sensitive, simple and rapid. Assay techniques include radioimmunoassays, enzyme immunoassays, cytotoxicity assays, and plaque assays.

CELL PROPAGATION AND ANTIBODY PRODUCTION

Once the desired fused cell hybrids have been selected and cloned into individual antibody-producing cell lines, each cell line can be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines can be propagated in vitro in laboratory culture vessels. The culture medium, containing high concentrations of a single specific monoclonal antibody, can be harvested by decantation, filtration or centrifugation.

USE OF THE MONOCLONAL ANTIBODY

The monoclonal antibodies made by the method of the subject invention can be utilized in any technique known or to be developed in the future that utilizes a monoclonal antibody.

A major use of monoclonal antibodies is in an immunoassay, which is the measurement of the antigen-antibody interaction. Such assays are generally heterogeneous or homogeneous. In a homogeneous immunoassay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and so forth. The major advantage of a homogeneous immunoassay is that the specific antibody need not be separated from the labeled analyte.

In a heterogeneous immunoassay, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen Means for producing a detectable signal include the use of radioactive labels, fluorescers, enzymes, and so forth. Exemplary of heterogeneous immunoassays are the radioimmunoassay, immunofluoroescence methods, enzyme-linked immunoassays, and the like.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

Another major use of monoclonal antibodies are in vivo imaging and therapeutics. The monoclonal antibodies can be labelled with radioactive compounds, for instance, radioactive iodine, and administered to a patient intravenously. The antibody can also be labelled with a magnetic probe. NMR can then be utilized to pinpoint the antigen. After localization of the antibodies at the antigen, the antigen can be detected by emission tomographical and radionuclear scanning techniques, thereby pinpointing the location of the antigen.

By way of illustration, the purified monoclonal antibody is suspended in an appropriate carrier, e.g., saline, with or without human albumin, at an appropriate dosage and is administered intravenously, e.g., by continuous intravenous infusion over several hours, as in Miller et al. In Hybridomas in Cancer Diagnosis and Therapy (1982), incorporated herein by reference.

The monoclonal antibodies of subject invention can be used therapeutically. Antibodies with the proper biological properties are useful directly as therapeutic agents. Alternatively, the antibodies can be bound to a toxin to form an immunotoxin or to a radioactive material or drug to form a radiopharmaceutical or pharmaceutical. Methods for producing immunotoxins and radiopharmaceuticals of antibodies are well-known (see, for example, *Cancer Treatment Reports* (1984) 68:317-328).

It also is believed that polyclonal antibodies derived from a germfree animal also can be utilized in immunoassays and provide an improved result as compared to polyclonal antibodies derived from a conventional animal. Polyclonal antibodies derived from a germfree animal can be made by utilizing a germfree animal, as described hereinabove, and immunization techniques, as described hereinabove, followed by separating the polyclonal antibodies from the animal by conventional techniques, e.g. by separating the serum from the animal.

A FIBRIN-SPECIFIC MONOCLONAL ANTIBODY

BACKGROUND

The hemostatic mechanism is a complex physiological response mechanism involved in repairing damage to a ruptured blood vessel. Hemostasis is achieved through the co-operative interactions among the wall of the damaged blood vessel, the platelets and the coagulative system. The role of the coagulation system is to provide an extensive fibrin network to stabilize and anchor the platelet plug which has been assembled on the subendothelial structure of the damaged vessel. The formation of the insoluble fibrin matrix from circulating fibrinogen is the result of a complex sequence of reactions culminating in the explosive production of thrombin at the required site. Coagulation is an amplification process involving a chain of enzymatic reactions in which proenzymes (clotting factors) are activated sequentially to active enzymes. There are a number of physiological mechanisms controlling the fibrin polymerization process involved in thrombus formation. These include the thrombin inhibitor antithrombin III (ATIII), protein C, prostacyclin and various components of the fibrinolytic system such as tissue plasminogen activator (t-PA) and its fast acting inhibitor (PAI).

The homeostasis hypothesis proposed by Astrup in 1956 Astrup, T., *Blood* 11, 781-806 (1956) states than equilibrium exists between fibrin formation (coagulation) and fibrin dissolution (fibrinolysis). In the normal or healthy state these functions are evenly balanced. However, when the hemostatic process is impaired, coagulation and fibrinolysis are pathologically expressed as thrombosis and hemorrhage, respectively. The clinical manifestations of pathological thrombosis or thrombotic disease are extremely diverse and include disseminated intravascular coagulation (DIC), deep vein thrombosis (DVT), arterial and venous thrombosis. Thromboembolism and thrombotic complications of other vascular disease (e.g. atherosclerosis) can result in occlusion of major arteries leading to organ ischemia and the attendant life-threatening conditions such as cerebrovascular accident (stroke), myocardial infarction, etc.

The fibrinolytic process involves the conversion of an inactive zymogen, plasminogen, to the proteolytic enzyme, plasmin, through the action of agents known as plasminogen activators. The molecular mechanism of physiological fibrinolysis is not fully understood, but it is known that during fibrin formation plasminogen binds to fibrin where it can be activated by plasminogen activators, e.g. t-PA. In this manner plasmin generation proceeds within the thrombus where it is protected from inactivation by the main physiological inhibitor of plasmin, alpha$_2$-antiplasmin.

Upon exposure to plasmin, fibrinogen and fibrin are broken down to their degradation products. Fibrinogen breaks down into fragments X and Y, and upon further exposure to plasmin, fragments D and E. Fibrin breaks down to fragments X, Y, D and E from non-crosslinked fibrin and crosslinked D-dimer, D-D/E complex, Y dimer, Y-D-dimer and X oligomer from crosslinked fibrin.

Assays for markers of thrombotic disorders have been conducted until quite recently using polyclonal antibodies in both radioimmunoassays and latex agglutination type assays. These assays have been demonstrated to be extremely unreliable by Gaffney (Gaffney, P. J., *Ann. N.Y. Acad. Sci.*, 408, 407-423 (1983). More specific and sensitive immunoassays (such as ELISAs) using monoclonal antibodies are becoming common practice in clinical laboratories. The limiting factor in these diagnostic assays is the specificity and affinity of the particular monoclonal antibody employed. The generation of highly specific antibodies to any of the potential indicators of impaired hemostasis is hampered by both low levels of indicators and the antigenic relatedness of the particular marker with its precursor, which is normally present at much higher levels in plasma. Examples are the formation of complexes between enzymes and their inhibitors e.g. thrombin-antithrombin III, plasmin-alpha$_2$-antiplasmin, t-PA-PAI-1. The number of new antigenic sites generated by such complex formation is extremely small and makes the production of immunological probes (such as monoclonal antibodies) difficult.

Likewise, the major problem associated with the acquisition of a monoclonal antibody to fibrin has been the structural and conformational similarities between fibrin and its physiological precursor fibrinogen. It has been estimated that the conservation of covalent structure when fibrinogen is converted to fibrin is greater that 98% (Plow, E. F., et al., *Semin. Thromb. Haemostas*, 8, 36 (1982) and, therefore, only a small percentage of the epitopes on the fibrin molecule are in fact neoantigens (and unique to fibrin). Many of the approaches which have been adopted to acquire fibrin antibodies have concentrated on immunizing animals with soluble fibrin fragments and synthetic peptides which mimic exposed neoantigenic sites on fibrin. See Hui, K. Y., et al., *Science* 22, 1129-32 (1983), Scheefers-Borchel, V., et al., *Proc. Natl. Acad. Sci USA*, 82,7091-95(1985), Elms, M. J., et al., *Thromb. Haemostas*, 50, 591-94 (1983, and Kurdryk, B., et al., *Mol. Immul.*, 21, 89-94 (1984). However, it is believed that the binding site of such antibodies is conserved during the fibrin degradation process and, therefore, such antibodies also can bind to fibrin degradation products.

The subject invention permits one to take a completely different approach and utilizes the intact fibrin antigen in conjunction with the enhanced immunological sensitivity of the antigen free (AF) animal to produce a fibrin-specific monoclonal antibody. For the purpose of the subject invention, a fibrin-specific monoclonal antibody binds to fibrin and not to fibrinogen, the fibrinogen degradation products or the fibrin degradation products.

MATERIALS AND METHODS

ANIMALS

Germfree BALB/cAnN mice were obtained from the germfree (GF) colony maintained at the University of Wisconsin. The animals were transported to our facility under GF conditions. The Antigen-Free (AF) colony was initiated by moving pregnant GF mice fed a natural ingredient diet L-485 (See Pleasants, J. P., et al., J.Nutr. 116, 1949-1964 (1986)) to an AF isolator where the mice were immediately transferred to the chemically defined (CD) AF diet. Their offspring, which had never directly contacted a Natural Ingredient (NI) diet, were weaned from maternal milk to CD diet and were designated the first AF generation. The AF mice were mated in pairs until the female was noticeably pregnant; then the male was removed to ensure that the female would thereafter receive her full daily lipid supplement. Young were weaned at 24 days of age.

HOUSING

AF breeders were housed in pairs in one half of a standard polycarbonate mouse cage 28×17.8×12.7 cm. The bottom had been cut out and replaced with a false bottom of mesh stainless steel. A longitudinal divider of sheet stainless steel was bolted to the ends of the plastic cage, projecting enough above and beyond the cage to hold in place a lid of stainless wire. This recessed lid, which normally fits inside a cage, was inverted to provide more adequate head room above the false bottom. Stainless steel collars of appropriate size were welded to the top of the lid to hold 60 mL diet bottles. Four stainless steel cups were welded to the sides of the longitudinal divider at the ends, halfway between the false bottom and the top. (A picture of the cages appears in Pleasants, J. R., The germfree system for aging and immunity In: CRC Handbook of Immunology in Aging, (Kay, M. M. B. S. Makinodan, T., eds.), pp. 257-297, CRC Press, Boca Raton, Fla. (1981). The diet bottles were of brown glass. Both diet and water bottles had plastic lids with holes drilled in their centers. The bottles were filled and inverted in their collars. The lipid supplement was measured daily into the stainless steel cups. A plastic pan was placed under each cage to receive wastes.

The filter paper which served both as bedding and as ingestible fiber was Whatman ashless filter paper No. 41, purchased as clippings (Sargent Welch). For bedding the paper was cut into strips. Uncut squares of the paper were used for cleanup inside the isolator. The paper was autoclaved for 25 min at 121'C, or was irradiated (4.5 Mrad) in plastic bags. All mice received enough paper to cover one end of the cage. It was replaced when it became wet, yellow or dirty.

The cages were maintained inside a 1.37×0.6×0.6M flexible isolator of the Trexler type (Trexler, P. C., Lab. Anim. Care, 13, 572-581 (1963)), using standard gnotobiotic technology (see Wostmann, B. S., Ed., Gnotobiotes Standards and Guide Lines for the Breeding, Care and Management of Laboratory Animals, National Research Council, National Academy of Sciences, Washington, D.C.) The isolators were maintained in a room at 21'C on a 12 h light dark schedule. A 2.5 cm diameter Tygon tube 7.55 cm long was sealed to the top of the isolator and closed with vinyl stoppers at both top and bottom. This provided an entry for sterile filtration of diet, water and oil.

DIET

Table 1 indicates both diet composition and the sequence for dissolving the ingredients in ultrafiltered Milli-Q water (Millipore, Mass.). The amino acids and dextrose were Sigma tissue culture grade. Vitamins were also from Sigma except for pure retinyl palmitate, kindly supplied by Hoffman-La Roche, Inc. (Nutley, N.J.). The other reagents were Fisher certified or equivalent. The complete water soluble diet was filtered cold through an Amicon Diaflo TC3 ultrafilter using three Pm10 membranes 150 mm in diameter (Amicon).

The ultrafilter membranes had a molecular weight cut off of 10,000 daltons. The assembled ultrafilter apparatus was sterilized before use by passing a 0.15% sodium hypochlorite solution through it, followed by thorough washing. Ultrafiltered diet was stored at 4~C in sterile reservoirs until needed. The diet was introduced into the AF isolator using a 0.2 um Nylon (MSI) filter in an autoclaved pressure filter holder with its delivery tube inserted into a No 6 Neoprene stopper. For this purpose, the upper vinyl stopper was removed from the Tygon tube sealed to the top of the isolator, and the interior of the tube was sprayed with a sterilizing solution of 2% peracetic acid containing 0.1% alkylaryl sulphonate. The filter holder stopper was inserted in place of the upper stopper. After 20 minutes the lower stopper was removed (inside the isolator) and diet or water was filtered into the isolator under 20 psi of nitrogen.

The composition of the lipid supplement is given in Table 2. The soy triglycerides were a preparation made from those methyl esters which vacuum distilled over a temperature range yielding the esters from palmitate to linolenate. These esters were then transesterified with glycerol to form the mixed triglycerides. (Nu-Chek Prep, Elysian, Minn.). The fat-soluble vitamins were added to the triglyceride mixture before its filtration into the isolator at which time it was warmed to 50~C and filtered into the isolator by the same procedure used for the water-soluble portion of the diet.

The lipid intake was a measured 0.375 ml/day. Increasing the lipid supplement has greatly decreased the mortality rate of newborn mice. The average litter size has also increased to that of conventionally reared animals. Lactating females received twice the normal amount of lipid supplement.

TABLE 1

Composition and preparation of chemically defined diet L489E1Se

| Ingredient | Amount (grams/100 grams of Ingredient) |
|---|---|
| To 192 ml Milli-Q water 70~C. the following were added: | |
| Leucine | 1.9 |
| Phenylalanine | 0.74 |
| Isoleucine | 1.08 |
| Methionine | 1.06 |
| Tryptophan | 0.37 |
| Valine | 1.23 |
| Asparagine | 0.91 |
| Arginine HCl | 0.81 |
| Threonine | 0.74 |
| Lysine HCl | 1.77 |
| Histidine HCl | 0.74 |
| The solution was cooled to 45~C. and the following added: | |
| Glycine | 0.59 |
| Proline | 1.48 |
| Serine | 1.33 |
| Alanine | 0.59 |
| Sodium glutamate | 3.40 |
| L-tyrosine ethyl ester HCl | 0.62 |
| Ferrous gluconate | 0.05 |
| Salts 35D[1] | 0.105 |
| Sodium Selenite[2] | 0.074 |
| Solution cooled to 5~C. and the following added: | |
| Calcium glycerophosphate | 5.22 |
| Magnesium glycerophosphate | 1.43 |
| Calcium chloride 2H$_2$O | 0.185 |
| Sodium chloride-Potassium Iodide (KI) mix (containing 680 mg KI) | 0.086 |
| Vitamin B mix 111E5[3] | 0.09 |
| Vitamin B12[4] | 120 mg |
| Choline chloride | 0.31 |
| Potassium acetate | 1.85 |
| To 108 ml Milli-Q water at 70° C. | |
| D-Dextrose, anhydrous was added | |
| Solutions cooled to 5° C. and combined both for ultrafiltration. | |

[1]Composition of salts 35D mixture given in Table 3
[2]Added in addition to sodium selenite in Salts 35D
[3]Composition of vitamin B mix 111E5 (see Table 4)
[4]Added in addition to vitamin B-12 in vitamin B mix 111E5

TABLE 2

Composition of lipid supplement LADEK 69E6

| Ingredient | Amount per daily dose* (0.375 ml) |
|---|---|
| Purified soy triglycerides[1] | 0.33 g |
| Retinyl palmitate | 6.45 mg (11.7 I.U.) |
| Cholecalciferol | .0288 mg (1.15 I.U.) |
| 2 ambo-alpha-tocopherol | 3.3 mg |
| 2 ambo-alpha-tocopherol acetate | 6.6 mg |
| Phylloquinone | 72 mg |

*Lactating mice received twice the normal adult dose.
[1]Consisting of:  12% palmitate
　　　　　　　　1.5% stearate
　　　　　　　　24% oleate
　　　　　　　　55% linoleate
　　　　　　　　8% linolenate

TABLE 3

Composition of the 35D Salts Mixture

| Salt | Amount (per 300 ml of diet) (mg) |
|---|---|
| Mn(acetate)$_2$ 4H$_2$O | 55.4 |
| ZuSO$_4$ H$_2$O | 40.6 |
| Cu(acetate)$_2$ H$_2$O | 3.7 |
| Cr(acetate)$_3$ H$_2$O | 2.5 |
| NaF | 2.1 |
| SnSO$_4$ 2H$_2$O | 0.37 |
| (NH$_4$)$_6$ Mo$_7$O$_{24}$ 4H$_2$O | 0.37 |
| NiCl$_2$ 3H$_2$O | 0.37 |
| Co(acetate)$_2$ 4H$_2$O | 0.11 |
| Na$_3$VO$_4$ | 0.22 |
| Na$_2$SeO$_3$ | 0.096 |

TABLE 4

Composition of the Vitamin B Mixture 111E5

| Ingredient | Amount (mg)/300 ml Diet) |
|---|---|
| Thiamine HCl | 1.23 |
| Pyridoxine HCl | 1.54 |
| Biotin | 0.25 |
| Folic Acid | 0.37 |
| Vitamin B12 | 0.37 |
| Riboflavin | 1.85 |
| Niacinamide | 9.2 |
| i-inositol | 61.9 |
| Calcium pantathenate | 12.3 |

Water was Milli-Q ultrafiltered grade and was filtered into the isolator in the same manner as the diet.

MICROBIOLOGICAL MONITORING

The antigen-free system was tested for microbial contamination according to guidelines set out in Wostmann, B. S. ed. (1970) Gnotobiotics Standards and guidelines for the breeding care and management of laboratory animals, National Research Council, National Academy of Sciences, Washington, D.C. Briefly, swabs wetted with diet and water from inside the isolator were used to obtain fecal smears obtained fresh from the mouse and from the accumulated waste under each cage. Smears were also taken from the walls of the isolator particularly around the entry ports. Duplicate smears were always taken. One set was tested by direct microscope examination for bacteria and fungi, using a gram stain. The second set of swabs was used for detection of microorganisms. Three weeks were allowed to elapse before a culture was considered to be negative.

Microbiological testing was performed approximately every two weeks or a few days after a new entry to the isolator had been made.

THE PRODUCTION OF MONOCLONAL ANTIBODIES USING ANTIGEN-FREE MICE

The antigen-free mice described hereinabove were used as the lymphocyte donor in the production of monoclonal antibodies. Solutions of all antigens were prepared under sterile conditions in a laminar flow hood.

The following protocol was adopted for the immunization of the AF mice. The antigen (25–50 micro g) was dissolved in sterile saline (100 micro 1) and emulsified with an equal volume of Freund's Complete Adjuvant (FCA). Interferon (1000 units) was added to the solution of antigen prior to the preparation of the emulsion. Sterile syringes and needles were used for all immunizations. The syringes were transferred to the AF isolator via the entry port where they were sterilized by spraying with a solution of peracetic acid (2%). Booster injections were given using the same amount of antigen and the replacement of FCA with Freund's Incomplete Adjuvant. A total of three booster immunizations were given each at intervals of three weeks. The final boost (without adjuvant) was given 4–7 days prior to fusion. All immunizations were given intraperitoneally. The mice were removed from the isolator on the day of the fusion and were immediately sacrificed by $CO_2$ asphyxiation. The spleens were removed and the splenocytes fused with mouse myeloma cells (NSI) using standard hybridoma technology.

USE OF THE ANTIGEN-FREE ANIMAL SYSTEM FOR THE PRODUCTION OF A FIBRIN-SPECIFIC MONOCLONAL ANTIBODY

The antigen-free system was used to generate a fibrin-specific monoclonal antibody. The antibody is highly specific and does not recognize fibrinogen, fibrin degradation products or fibrinogen degradation products. The hybridoma cell line was produced by fusion of splenocytes from antigen free BALB/c mice, immunized with human fibrin, and NSI myeloma cells.

IMMUNIZATION SCHEDULE

Three eight week old female antigen free mice were immunized with 33 micrograms of a human fibrin preparation. The preparation was a freeze fracture sample of fibrin which was prepared as follows:

Human fibrinogen was converted to fibrin by thrombin and Factor XIIIa. The fibrin clot was then frozen in liquid nitrogen and reduced to an extremely fine powder by mechanical disruption. A dispersion of the freeze fractured fibrin was made in saline to give a clear solution of crosslinked fibrin XL-Fn with a final concentration of 1 mg/mL. 33 microL of this fibrin antigen was used to immunize the animals. The volume of the antigen solution was adjusted to 100 microL with sterile saline and was then emulsified with FCA as described in the last section. Two booster immunizations were administered, at intervals of three weeks, using the same level of antigen in Freund's Incomplete Adjuvant. The final booster was given 4 days prior to the fusion. The same level of antigen was used and adjuvant was replaced with saline.

DETECTION AND DETERMINATION OF ANTIBODY

Qualitative and quantitative determinations of monoclonal antibody were performed using an enzyme linked immunosorbent assay (ELISA). The ELISAs were performed using human fibrin immobilized onto a 96 well PVC plate (Costar). The fibrin coated assay plates were prepared by incubating 100 microL of a fibrinogen solution (Kabi, grade L) (50 micrograms/mL borate/saline buffer) overnight at 4° C. Unbound fibrinogen was removed by washing with PBS containing 0.05% Tween 80 (PBS-Tween). The fibrinogen coated onto each plastic well was converted to fibrin by incubation with 100 microliters of a thrombin solution (10 NIH units/ml) containing 2 $mMCaCl_2$ for 1 hour at 37° C. Standard calibration curves for the antibody were constructed using a preparation of antibody which was homogeneous by SDS-PAGE.

To prevent non-specific binding, the fibrin coated plates were incubated with a 1% solution of BSA in PBS pH7.4. Antibody containing solutions (100 microL) were then added and incubated at 37~C for 90 minutes. After each step in the procedure the wells were extensively washed with PBS-Tween. Bound antibody was detected by the addition of a 1000 fold dilution of rabbit anti-mouse antibody conjugated to alkaline phosphatase (Sigma) diluted in PBS, 1% BSA pH8.0.

PRODUCTION OF HYBRIDOMAS—FUSION

The mice were sacrificed by $CO_2$ asphyxiation and a splenectomy performed immediately. The spleen cells from the immunized mice were fused with the fusagent polyethylene glycol 4000 (3000–3700). The cells were incubated in HAT selection media in T flasks for 1 week. After this time the cells were plated out into 5×96 well plates from which 93 wells showed growth. Of these, 19 wells were positive for the fibrin antigen. One of these clones, F492D8 (later renamed MH1), produced antibody which recognized the fibrin antigen but did not crossreact with fibrinogen. This particular clone, MH1, was recloned three times by limiting dilution with the tertiary cloning phase performed at 1 cell per well. Once the cell line was stabilized it was weaned onto a serum-free medium the cell line produces antibody at the level of approximately 7.5 mg/liter.

PURIFICATION OF MONOCLONAL ANTIBODY

Before purification (4 Liter batches of) tissues culture supernatants were centrifuged to remove cellular debris and filtered through a 0.8 microM nylon membrane to remove any residual particulate material. The hybridoma supernatant was concentrated at 4~C to a volume of 500 mL using a spiral wound ultrafiltration system employing a YM type membrane (Amicon) with molecular weight cut of 30,000. Buffer exchange to 20 mM 2(N-morpholine) ethane sulphonic acid (MES), pH6 (Buffer A) was accomplished by diafiltration according to the manufacturers instructions. After further concentration to a final volume of 100 ml, the antibody solution was filtered through a 0.451 micron nylon membrane before further purification. The concentrated antibody solution was purified by liquid chromatography on a Waters HPLC chromatograph using a 7.75 mm ×10 cm ABx column (J. T. Baker, Phillipsburg, N.J.). The column was equilibrated with buffer A and the sample (100 ml) was applied at a flow rate of 1.0 ml/min. After extensive washing with buffer A the antibody was eluted from the column with a gradient from buffer A to 100% buffer B (1M sodium acetate pH7) at 1 ml/min. Fractions (2ml) were collected and those containing MAb (as determined by ELISA) were pooled and dialysed against phosphate buffer saline (PBS) (20 mM sodium phosphate, 150 mM sodium chloride, pH7.4) and stored at −20° C. at concentrations >1 mg/ml. The ABx column was regenerated by washing for 5 minutes with 100% buffer B, followed by re-equilibration with 15 column volumes of buffer A.

DETERMINATION OF FIBRIN SPECIFICITY

Initial determination of fibrin specificity was achieved by screening hybridoma supernatants separately on fibrin and fibrinogen coated microtiter plates. Only those cell lines producing antibody that did not crossreact with fibrinogen were accepted.

Further confirmation of fibrin specificity was determined utilizing a competition assay with fibrinogen in solution, thereby confirming that the antibody does not recognize fibrinogen in solution.

The competition assay employed to ascertain the fibrin specificity of the antibody was performed as described for the ELISA assay hereinabove with preincubation of the antibody with fibrinogen in solution. Briefly, hybridoma supernatant was incubated at 37° C. for 30 minutes with solutions of fibrinogen at physiological concentrations (4 mg/ml) containing BSA (10 mg/ml) to prevent non specific binding of antibody to fibrinogen. The fibrinogen/antibody solution was then transferred to wells of a microtiter plate which had been coated with fibrin. GlyProArgPro (GPRP) was added to the fibrinogen inhibitor to prevent possible polymerization of fibrinogen by residual thrombin in the fibrin wells. The assay is then performed as a conventional ELISA assay for antibody bound to an immobilized antigen. In all experiments to test the fibrin specificity of the MHI antibody a second antibody 45J was used as a control. 45J crossreacts with fibrin and fibrinogen.

DETERMINATION OF CROSSREACTIVITY WITH FIBRINOGEN

IMMOBILIZED FIBRIN AND FIBRINOGEN

The cell line MHI produces a murine monoclonal antibody which crossreacts with fibrin when it is immobilized on the surface of a PVC microtiter assay plate (table 5). In the same assay the antibody does not recognize fibrinogen immobilized on the plate. As the data on table 5 indicate, there is a dramatic increase in immunoreactivity once fibrinogen is converted to fibrin by thrombin, indicating clearly the exposure or formation of a neoepitope on the fibrin molecule. The control antibody, 45J, however clearly recognizes an epitope which is conserved when fibrinogen is converted to fibrin.

COMPETITION ASSAY WITH FIBRIN AND FIBRINOGEN

The fibrin specificity of the antibody, MHI antibody, was further demonstrated in a competition assay in which hybridoma supernatant was preincubated with a fibrinogen solution (final concentration of 4 mg/ml) prior to an ELISA on fibrin coated wells. Since such a high level of fibrinogen was used in this competition assay (×500 that of the antibody concentration) BSA (10 mg/ml final concentration) was added to the mixture. The peptide GPRP was added to prevent fibrin polymerization by residual thrombin on the fibrin coated wells. The results of this assay indicate that the MH1 antibody does not recognize fibrinogen in solution (Table 6).

Assuming 400 ng. of fibrin binds to each well of the microtiter assay plate, then the fibrinogen level used in this particular competition assay represents a 1,000 fold excess over the bound fibrin antigen. In addition it represents a 400 fold excess of the antibody level in the tissue supernatant.

TABLE 5

| Crossreactivity of MH1 Antibody with Fibrinogen and Fibrin Antigen | | |
|---|---|---|
| | $A_{405\ nM}$/30 min. | |
| MAb | Fibrin | Fibrinogen |
| MH1 | .90 | .025 |
| 45J | 1.65 | 1.50 |

TABLE 6

| Crossreactivity of MH1 Antibody with Fibrin in the Presence of Fibrinogen | | |
|---|---|---|
| | $A_{405\ nM}$/30 min. | |
| MAb | + fibrinogen | − fibrinogen |
| MH1 | 1.24 | 1.27 |
| 45J | 0.438 | 1.74 |

DETERMINATION OF CROSSREACTIVITY WITH FIBRIN(OGEN) DEGRADATION PRODUCTS

Fibrinogen degradation products (FDPs) were prepared by incubating fibrinogen with plasmin at 37° C. for time periods ranging from 10 minutes to 3 hours. At the desired time fibrinogenolysis was stopped by the addition of Trasylol (100 Kallikrein inhibitor units/mL) and 20 mM epsilon amino caproic acid (EACA).

Crosslinked fibrin degradation products (XLFDPs) were prepared by the addition of thrombin (4 NIH units/mL) to a fibrinogen solution (5 mg/mL) in Tris buffered saline (TBS, pH 7.4, 50 mM Tris HCl, 150 mM NaCl) containing 10 mM $CaCl_2$, plasminogen (0.25 mg/mL) and urokinase (50 IU/mL). The mixture was incubated at 37° C. and the plasmin digestion terminated at different time intervals as described hereinabove for the FDPs.

To determine crossreactivity of the antibody with fibrin degradation products and fibrinogen degradation products the appropriate degradation products were coated onto microtiter plates and ELISAs were performed by conventional methods. As the results in Table 7 indicate, the MH1 antibody does not crossreact with any plasmin generated fibrinogen degradation products. As table 8 indicates, the antibody does not react with XL-fibrin degradation products. This observation also was made when the antibody was tested for crossreactivity by Western blotting analysis.

The conclusion can be drawn that the antibody recognizes an epitope of the intact fibrin molecule which is not present or exposed on the surface of the precursor molecule, fibrinogen. The epitope is apparently destroyed by plasmin digestion of crosslinked fibrin as the data in table 8 suggest.

Accordingly, the MH1 antibody is a fibrin-specific monoclonal antibody which can be defined as follows:

For the purpose of the subject invention a fibrin-specific monoclonal antibody is a monoclonal antibody that:

1. in a competition assay to measure crossreactivity with fibrin and fibrinogen, as described hereinabove, the monoclonal antibody has less than about 75%, and preferably less than about 10%, crossreactivity with fibrinogen when fibrinogen is utilized in a quantity of a 1,000 fold excess as compared to fibrin,
2. in an assay to measure crossreactivity with crosslinked fibrin and fibrin degradation products, as described hereinabove, the reactivity of the monoclonal antibody with the fibrin that has been digested with plasmin for about three hours is less than about 50%, and preferably less than about 40%, of the reactivity of the monoclonal antibody with fibrin at time zero, and
3. in an assay to measure crossreactivity with fibrinogen and fibrinogen degradation products, as described hereinabove, the reactivity of the monoclonal antibody with fibrinogen that has been digested with plasmin for about four hours is no greater than the reactivity of the monoclonal antibody with fibrinogen at time zero.

The MHI antibody has been further characterized by determining its affinity for fibrin. The affinity was determined by Scatchard analysis (Frankel et al., *Molecular Immunology*, 16, 101–106(1979)) using 125I-labelled MH1 antibody. The value obtained for the dissociation constant $K_D$ was $6.7 \times 10^{-10}$ M. Such affinity is about 5,000 times that of the affinity of t-PA for fibrin.

It has also been determined by Western Immunoblotting analysis that the MH1 antibody does not crossreact with the $A\alpha$, $B\beta$ or gamma chains of fibrinogen. Also, it has been determined by the same method of analysis that the MH1 antibody does not crossreact with thrombin treated $A\alpha$ or $B\beta$ chains of fibrinogen. (Thrombin treatment of fibrinogen results in the release of fibrinopeptide A and fibrinopeptide B from the $A\alpha$ chain and $B\beta$ chain, respectively, therefore forming the $\alpha$ chain and $\beta$ chain of fibrin.)

TABLE 7

Crossreactivity of MH1 Antibody with Fibrinogen Degradation Products

| Plasmin Digestion Time (mins) | $A_{405\,nm/30\,min}$ MH1 | 45J |
|---|---|---|
| 0 | 0.15 | 1.037 |
| 10 | 0.10 | nm |
| 20 | 0.11 | 1.02 |
| 40 | 0.11 | 0.410 |
| 60 | 0.10 | 0.330 |
| 240 | 0.09 | 0.300 |

TABLE 8

Crossreactivity of MH1 Antibody with Fibrin Degradation Products

| Plasmin Digestion Time (hours) | $A_{405\,nm/30\,min}$ MH1 | 45J |
|---|---|---|
| 0 | 0.890 | 1.40 |
| 3 | 0.354 | 1.0 |
| 5 | 0.310 | 0.77 |

In addition, as the results in Table 7 indicate, the control antibody, 45J antibody, binds to fibrinogen and does not crossreact with fibrinogen degradation products. Accordingly, such a monoclonal antibody is a fibrinogen-specific monoclonal antibody and represents another aspect of the subject invention. The fibrinogen-specific monoclonal antibody can be utilized in any immunoassay that can be utilized to determine plasma fibrinogen levels in vitro. The 45J antibody has been further characterized in that it has been determined that the 45J epitope is on the $A\alpha$ chain of fibrinogen in the region from about amino acid 206 to about 424 and most likely in the region from about amino acid 207 to about 231. For the purpose of the subject invention, a fibrinogen-specific monoclonal antibody is an antibody that in an assay to measure crossreactivity with fibrinogen and fibrinogen degradation products, as described hereinabove, the reactivity of the monoclonal antibody with fibrinogen that has been digested with plasmin for about 40 minutes is less than about 50% of the reactivity of the monoclonal antibody with fibrinogen at time zero.

The 45J hybridoma was made by conventional techniques utilizing a conventional Balb/c mouse wherein the mouse was immunized with fibrin. However, fibrinogen also can be utilized as the antigen.

DETERMINATION OF CROSS REACTIVITY WITH NONCROSSLINKED FIBRIN AND NONCROSSLINKED FIBRIN CLOTS

It has been demonstrated by ELISA that the antibody MH1 crossreacts with not only crosslinked fibrin (XLFn) but also noncrosslinked fibrin (NONXLFn). The ELISA was performed as follows:

1. 96 well microtiter assay plates were coated with 100 ul of a fibrinogen solution (50 ug/mL in borate (pH8.5) saline buffer) at 4° C. overnight.

2. Crosslinked fibrin was formed in the fibrinogen coated wells by incubation for 1 hour at 37° C. with a thrombin solution (10 NIH units/ml) in Tris buffered saline (TBS, pH 7.4, 50 mM Tris HCl, 150 mM NaCl), containing 2 mM $CaCl_2$ and 10 mM cysteine.

3. Noncrosslinked fibrin was formed in the fibrinogen coated wells by incubation for 1 hour at 37° C. with a thrombin solution (10 NIH units/ml) in phosphate buffer (pH 6.1) containing EDTA to a final concentration of 0.0125M.

4. The bound antibody was determined by incubation with an antimouse alkaline phosphatase conjugate. Bound conjugate was determined by the addition of an alkaline phosphatase substrate and the resultant colorimetric reaction monitored at 405 nM in an automatic plate reader.

The results of the assay are shown in Table 9 and it can be concluded that the antibody crossreactivity with crosslinked fibrin is greater than it is with noncrosslinked fibrin. The simplest explanation being that the covalent crosslinking present in the crosslinked polymeric structure serves to lock or freeze the conformation which the antibody recognizes. In the noncrosslinked species the conformation, although it is formed, it is not stabilized by covalent bonding of the polymer.

It has also been demonstrated that the antibody crossreacts with both crosslinked and noncrosslinked clots, formed in vitro. Crosslinked fibrin was prepared by incubating a fibrinogen solution (In Tris (50 mM, pH7.4) saline, containing $CaCl_2$ (2 mM) and cysteine (10 mM)) with thrombin (10 NIH units/ml) for 3 hours at 37° C. The noncrosslined fibrin was formed by incubating a fibrinogen solution (3 mg/ml) in phosphate buffer (pH6.1) containing EDTA to a final concentration of 0.0125M with a thrombin solution (10 NIH units/ml) for 3 hours at 37° C. After formation of the clots, they were washed and incubated at 37° C. with 400 ul of a 1% BSA solution containing $^{125}$Iodine-labelled MH1 antibody. Small aliquots of solution were removed at different time points and the amount of antibody uptake was determined by counting the plasma in a gamma counter.

Table 10 shows the uptake of antibody by both the noncrosslinked and crosslinked clots.

TABLE 9

Crossreactivity of MH1 Antibody with Crosslinked and Noncrosslinked Fibrin

| Antibody Concentration (ng./ml.) | Crosslinked Fibrin | Noncrosslinked Fibrin |
|---|---|---|
| | (Absorbance at 405 nanometers) | |
| 100.000 | 0.764 | 0.409 |
| 50.000 | 0.460 | 0.319 |
| 25.000 | 0.305 | 0.154 |
| 12.500 | 0.174 | 0.074 |
| 6.250 | 0.069 | 0.000 |

TABLE 10

Crossreactivity of MH1 Antibody with Crosslinked and Noncrosslinked Fibrin Clots

| Fibrin Clot | % Uptake of Labelled Antibody After 8 Hours |
|---|---|
| Crosslinked | 79% |
| Noncrosslinked | 76% |

DEPOSIT OF HYBRIDOMA

MH1 and 45J were deposited in the American Type Culture Collection (ATCC) on Jun. 9, 1988 and given accession number HB 9739 and HB 9740, respectively. The ATCC is located at 12301 Parklawn Drive, Rockville, Md. 20852. MH1 antibody is an IgG$_1$ antibody with a kappa light chain and it has been observed that the MH1 antibody crossreacts with not only human fibrin but also rabbit fibrin.

The subject invention is not intended to be limited in scope to the hybridomas deposited but they are intended as a single illustration of hybridomas that produced a fibrin-specific monoclonal antibody and a fibrinogen-specific monoclonal antibody, as defined herein. Any cell line that is functionally equivalent is within the scope of the subject invention. By the term "functionally equivalent" it is meant that an antibody is capable of competing with the MHI antibody or 45J antibody in binding to the epitope of fibrin to which the MHI antibody binds or to the epitope of fibrinogen to which the 45J antibody binds, respectively. In addition, such term includes fibrin-specific monoclonal antibodies and fibrinogen-specific monoclonal antibodies, as defined herein, that bind to an epitope different from that which the MHI antibody binds and the 45J antibody binds, respectively.

IN VIVO DIAGNOSTIC AND THERAPEUTIC USES FOR FIBRIN-SPECIFIC MONOCLONAL ANTIBODIES

CLOT/VASCULAR DISEASE LOCALIZATION

The fibrin-specific monoclonal antibodies of this invention are capable of targeting fibrin clots or aggregation of fibrin in vivo. They can, therefore, be used in humans for localization of possible tissue or vascular damage and for monitoring of vascular diseases. A fibrin-specific monoclonal antibody is particularly preferred for this use because such monoclonal antibody will not bind to fibrinogen, fibrin degradation products and fibrinogen degradation products, thereby reducing background, which permits one to more precisely localize the fibrin clot or aggregation of fibrin.

For this application, it is preferable to use purified monoclonal antibodies. Preferably, purification may be accomplished by HPLC methods. Purification of monoclonal antibodies for human administration may also be accomplished by ammonium sulfate or sodium sulfate precipitation followed by dialysis against saline and filtration sterilization. Alternatively, immunoaffinity chromatography techniques may be used to purify the monoclonal antibodies.

The purified monoclonal antibodies can be labelled with radioactive compounds, for example $^{123}$I, $^{125}$I, $^{131}$I, [99]mTc, $^{111}$In, and administered to a patient intravenously. The antibody also can be labelled with a magnetic probe. NMR can then be utilized to pinpoint the clot. After localization of the antibodies at the clot or fibrin aggregation they can be detected by emission tomographical and radionuclear scanning techniques thereby pinpointing the location of, for example, the thrombus or fibrin encapsulated tumor.

By way of illustration, the purified monoclonal antibody is suspended in an appropriate carrier, e.g., saline, with or without human albumin, at an appropriate dosage and is administered to a patient. The monclonal antibodies are preferably administered intravenously, e.g., by continuous intravenous infusion over several hours.

TREATMENT OF VASCULAR DISEASES WITH MONOCLONAL ANTIBODY CONJUGATES

The monoclonal antibodies of this invention can be used in conjunction with a broad range of pharmaceutical agents such as cytotoxic reagents and thrombolytic reagents, e.g. t-PA, urokinase streptokinase, and other proteases that are capable of lysing fibrin. Such use is particularly preferred because the fibrin-specific monoclonal antibodies of the subject invention permit a very efficient use of such reagents because none of the reagent will be lost by binding to fibrinogen, fibrin degradation products or fibrinogen degradation products. For various reviews on the subject, see Bale et al., 1980, *Cancer Research,* 40:2965-297; Ghose and Blair, 1978, *J.Natl. Cancer Inst.,* 61(3):657-676;

Gregoriadis, 1977, *Nature,* 265:407-411; Gregoriadis, 1980 *Pharmac. Ther.,* 10:103-108; and Trouet et al., 1980, *Recent Results Cancer Res.,* 75:229-235.

The methods used for binding these agents to the monoclonal antibody molecule can involve either non-covalent or covalent linkages. Since non-covalent bonds are more likely to be broken before the antibody complex reaches the target site, covalent linkages are preferred. For instance, a carbodiimide bond can be formed between the carboxy groups of the pharmaceutical agent and the amino groups of the antibody molecule. Bifunctional agents such as dialdehydes or imidoesters can be used to link the amino group of a drug to amino groups of the antibody molecule. The Schiff base reaction can be used to link drugs to antibody molecules. This method involves the periodate oxidation of a drug or cytotoxic agent that contains a glycol or hydroxy group, thus forming an aldehyde which is then reacted with the antibody molecule. Attachment occurs via formation of a Schiff base with amino groups of the antibody molecule. Additionally, drugs with reactive sulfhydryl groups have been coupled to antibody molecules.

We claim:

1. A method for production of a monoclonal antibody to an antigen comprising:
   (a) immunizing an antigen-free animal at least three times with said antigen to permit antibody-producing cells to produce antibodies to said antigen;
   (b) removing at least a portion of said antibody-producing cells from said antigen-free animal,
   (c) forming a hybridoma by fusing one of said antibody-producing cells with an immortalizing cell wherein said hybridoma is capable of producing a monoclonal antibody to said antigen,
   (d) propagating said hybridoma, and
   (e) harvesting the monoclonal antibodies produced by said hybridoma.

2. The method of claim 1 wherein said antigen-free animal is selected from the group consisting of a mouse, rat, pig, guinea pig, poultry, a goat, a sheep, primate and a rabbit.

3. The method of claim 2 wherein said antigen-free animal is a mouse.

4. The method of claim 3 wherein said mouse is a Balb/C mouse.

5. A method for production of polyclonal antibodies to an antigen comprising immunizing an antigen-free animal at least three times with said antigen to permit antibody producing cells to produce antibodies to said antigen and separating serum, which contains said polyclonal antibodies, from said animal.

6. The method of claim 5 wherein said antigen-free animal is selected from the group consisting of a mouse, rat, pig, guinea pig, poultry, a goat, a sheep, primate and a rabbit.

7. The method of claim 6 wherein said antigen-free animal is a mouse.

8. The method of claim 7 wherein said antigen-free animal is a Balb/C mouse.

* * * * *

UNITED STATES PATENT AND TRADEMARK OFFICE
CERTIFICATE OF CORRECTION

PATENT NO. : U.S. 5,223,410

DATED : June 29, 1993

INVENTOR(S) : Paul E. Gargan, Victoria A. Ploplis, Julian R. Pleasants

It is certified that error appears in the above-identified patent and that said Letters Patent is hereby corrected as shown below:

Column 4, at line 7, after "[ed].", "the" should read --The--; at line 61, "conceivable" should read --conceivably--.

Column 7, at line 48, after "[ed].", ". the" should read --The--.

Column 8, at line 13, "a tocopherol should read --$\alpha$ tocopherol--; at line 23, "MN" should read --Mn--; at line 45, "121~C" should read --121°C--; at line 46, "250~F" should read --250°F--.

Column 11, at line 12, "hysterotomy" should read --hysterectomy--; at line 24, "Hysterotomy" should read --Hysterectomy--; at line 46, "UFAQ" should read --UFAW--.

Column 12, at lines 56-58, "(grams/100 grams of Ingredient)" should read --(g/100 g water-soluble nutrients)--; at line 59, "70~C" should read --70°C--; at line 69, "Histidine HCl" should read --Histidine HCl•$H_2O$--.

Column 13, at lines 5-7, "(grams/100 grams of Ingredient)" should read --(g/100 g water-soluble nutrients)--; at line 8, "45~C" should read --45°C--; at line 16, "5~C" should read --5°C--; at line 19, delete "0.086"; at line 20, "680 mg KI" should read --680 $\mu$g KI--; at line 25, "70~C" should read --70°C--; at line 28, "sodium selenate" should read --sodium selenite--; at line 39, "6.45 mg" should read --6.45 $\mu$g--; at line 40, "0.0288 mg" should read --0.0288 $\mu$g--; at line 43, "72 mg" should read --72 $\mu$g--.

Column 20, at line 1, "121'C" should read --121°C--; at line 14, "21'C" should read --21°C--; at line 36, "4~C" should read --4°C--; at line 60, "50~C" should read --50°C--.

Column 21, at lines 5-6, "(grams/100 grams of Ingredient)" should read --(g/100 g water-soluble nutrients)--; at line 8, "70~C" should read --70°C--; at line 16, "Histidine HCl" should read --Histidine HCl•$H_2O$--; at line 17, "45~C" should read --45°C--; at line 25, "5~C" should read --5°C--; at line 30, "680 mg KI" should read --680 $\mu$g KI--; at line 47, "6.45 mg" should read --6.45 $\mu$g--; at line 48, ".0288 mg" should read --.0288 $\mu$g--; at line 51, "72 mg" should read --72 $\mu$g--; at line 60, "(per 300 ml of diet) (mg)" should read --(mg/100 g water-soluble solids)--; at line 62, "ZuSO$_4$H$_2$O" should read --ZnSO$_4$H$_2$O--; at line 64, "Cr(acetate)$_3$H$_2$O" should read --Cr(acetate)$_2$H$_2$O--.

UNITED STATES PATENT AND TRADEMARK OFFICE
CERTIFICATE OF CORRECTION

PATENT NO. : U.S. 5,223,410

DATED : June 29, 1993

INVENTOR(S) : Paul E. Gargan, Victoria A. Ploplis, Julian R. Pleasants

It is certified that error appears in the above-indentified patent and that said Letters Patent is hereby corrected as shown below:

Column 22, at line 4, "(per 300 ml of diet)(mg)" should read --(mg/100 g water-soluble solids)--; at line 11, "(mg)/300 ml Diet)" should read --(mg/100 g water-soluble solids)--.
Column 24, at line 33, "0.451 micron" should read --0.45 micron--.
Column 25, at lines 55 and 64, "nM" should read --nm--.
Column 28, at line 18, "nM" should read --nm--; at line 24, "explanation being" should read --explanation is--; at line 28, delete "it" (2nd occurrence) at line 36, "noncrosslined" should read --noncrosslinked--.

Signed and Sealed this

Fourth Day of June, 1996

Attest:

BRUCE LEHMAN

Attesting Officer

Commissioner of Patents and Trademarks